US009801647B2

(12) United States Patent
Rosenthal

(10) Patent No.: US 9,801,647 B2
(45) Date of Patent: Oct. 31, 2017

(54) CATHETER INCLUDING CUTTING ELEMENT AND ENERGY EMITTING ELEMENT

(71) Applicant: Covidien LP, Mansfield, MA (US)

(72) Inventor: Michael Rosenthal, San Carlos, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/674,581

(22) Filed: Nov. 12, 2012

(65) Prior Publication Data
US 2013/0123823 A1    May 16, 2013

Related U.S. Application Data

(63) Continuation of application No. 11/442,685, filed on May 26, 2006, now abandoned.

(51) Int. Cl.
*A61B 17/32* (2006.01)
*A61B 17/3207* (2006.01)
(Continued)

(52) U.S. Cl.
CPC ............... *A61B 17/32002* (2013.01); *A61B 17/320758* (2013.01); *A61B 17/320783* (2013.01); *A61B 17/320068* (2013.01); *A61B 2017/22039* (2013.01); *A61B 2017/22095* (2013.01); *A61B 2017/2905* (2013.01); *A61B 2017/2927* (2013.01); *A61B 2017/32004* (2013.01); *A61B 2090/0811* (2016.02); *A61B 2090/3784* (2016.02)

(58) Field of Classification Search
CPC ...... A61B 17/32002; A61B 17/320758; A61B 17/320783; A61B 17/320068; A61B 2017/22039; A61B 2017/2927; A61B 2017/32004; A61B 2017/2905; A61B 2017/22095; A61B 2019/528; A61B 2019/4857
USPC ........................................ 606/170, 159, 167
See application file for complete search history.

(56) References Cited

U.S. PATENT DOCUMENTS

| 1,481,078 | A | 1/1924 | Albertson |
| 2,178,790 | A | 11/1939 | Henry |

(Continued)

FOREIGN PATENT DOCUMENTS

| CA | 2000621 A1 | 4/1990 |
| DE | 3732236 C1 | 12/1988 |

(Continued)

OTHER PUBLICATIONS

Extended European Search Report regarding related European Patent Application No. 13172807.3, dated Aug. 23, 2013, 6 pages.

(Continued)

*Primary Examiner* — Corrine McDermott
*Assistant Examiner* — Tin Nguyen

(57) ABSTRACT

A catheter for removing tissue from a body lumen and for providing information relating to the body lumen. The catheter includes a tissue cutting element that rotates relative to the catheter body and is mounted to the drive shaft for imparting rotation to the tissue cutting element. An energy emitting element of the catheter rotates relative to the catheter body and is rotatable independently of the tissue cutting element.

10 Claims, 13 Drawing Sheets

(51) Int. Cl.
 *A61B 17/22* (2006.01)
 *A61B 17/29* (2006.01)
 *A61B 90/00* (2016.01)

(56) References Cited

U.S. PATENT DOCUMENTS

| | | |
|---|---|---|
| 2,701,559 A | 2/1955 | Cooper |
| 2,850,007 A | 9/1958 | Lingley |
| 3,064,651 A | 11/1962 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Willson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Blanko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom et al. |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,846,192 A | 7/1989 | MacDonald |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,889,061 A | 12/1989 | McPherson et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinski et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,011,490 A | 4/1991 | Fischell et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause |
| 5,078,722 A | 1/1992 | Stevens |
| 5,078,723 A | 1/1992 | Dance et al. |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,108,500 A | 4/1992 | Mattox |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,116,352 A | 5/1992 | Schnepp-Pesch et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |

(56) References Cited

U.S. PATENT DOCUMENTS

| | | |
|---|---|---|
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,261,877 A | 11/1993 | Fine et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,290,303 A | 3/1994 | Pingleton et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A * | 5/1994 | Shturman .................... 606/159 |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,336,167 A | 8/1994 | Sullivan et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,409,454 A | 4/1995 | Fischell et al. |
| 5,413,107 A | 5/1995 | Oakley et al. |
| 5,419,774 A | 5/1995 | Willard et al. |
| 5,421,338 A | 6/1995 | Crowley et al. |
| 5,423,799 A | 6/1995 | Shiu |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,466,382 A | 11/1995 | Downey et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,760 A | 4/1996 | Wynne et al. |
| 5,507,761 A | 4/1996 | Duer |
| 5,507,769 A | 4/1996 | Marin et al. |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,279 A | 10/1996 | Rainin |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,415 A | 4/1997 | Lucey et al. |
| 5,620,447 A | 4/1997 | Smith et al. |
| 5,624,457 A | 4/1997 | Farley et al. |
| 5,626,562 A | 5/1997 | Castro |
| 5,628,761 A | 5/1997 | Rizik |
| 5,632,754 A | 5/1997 | Farley et al. |
| 5,632,755 A | 5/1997 | Nordgren et al. |
| 5,643,296 A | 7/1997 | Hundertmark et al. |
| 5,643,298 A | 7/1997 | Nordgren et al. |
| 5,649,941 A | 7/1997 | Lary |
| 5,662,671 A | 9/1997 | Barbut et al. |
| 5,669,275 A | 9/1997 | Mills |
| 5,669,920 A | 9/1997 | Conley et al. |
| 5,669,926 A | 9/1997 | Aust et al. |
| 5,674,232 A | 10/1997 | Halliburton |
| 5,676,697 A | 10/1997 | McDonald |
| 5,681,336 A | 10/1997 | Clement et al. |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |

(56) References Cited

U.S. PATENT DOCUMENTS

| | | |
|---|---|---|
| 5,707,376 A | 1/1998 | Kavteladze et al. |
| 5,707,383 A | 1/1998 | Bays et al. |
| 5,709,698 A | 1/1998 | Adams et al. |
| 5,713,913 A | 2/1998 | Lary et al. |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,222 A | 11/1998 | Makower |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A * | 2/1999 | Powell et al. ............... 600/585 |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,361 A | 3/1999 | Nash |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,906,627 A | 5/1999 | Spaulding |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,941,869 A | 8/1999 | Patterson et al. |
| 5,947,985 A | 9/1999 | Imran |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,979,951 A | 11/1999 | Shimura |
| 5,985,397 A | 11/1999 | Witt et al. |
| 5,989,281 A | 11/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A * | 2/2000 | Brown et al. ............... 600/459 |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,066,153 A | 5/2000 | Lev |
| 6,068,603 A | 5/2000 | Suzuki |
| 6,081,738 A | 6/2000 | Hinohara et al. |
| RE36,764 E | 7/2000 | Zacca et al. |
| 6,095,990 A | 8/2000 | Parodi |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,006 B1 | 4/2001 | Dubrul et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,263,236 B1 | 7/2001 | Kasinkas et al. |
| 6,264,611 B1 | 7/2001 | Ishikawa et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,275 B1 | 11/2001 | Lashinski et al. |
| 6,330,884 B1 | 12/2001 | Kim |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |
| 6,425,870 B1 | 7/2002 | Flesch |
| 6,428,551 B1 | 8/2002 | Hall et al. |
| 6,428,552 B1 | 8/2002 | Sparks |
| 6,445,939 B1 | 9/2002 | Swanson et al. |
| 6,447,525 B2 | 9/2002 | Follmer et al. |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |

(56) References Cited

U.S. PATENT DOCUMENTS

| | | |
|---|---|---|
| 6,565,588 B1 | 5/2003 | Clement et al. |
| 6,569,177 B1 | 5/2003 | Dillard et al. |
| 6,592,526 B1 | 7/2003 | Lenker |
| 6,605,061 B2 | 8/2003 | VanTassel et al. |
| 6,610,059 B1 | 8/2003 | West, Jr. |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,627,784 B2 | 9/2003 | Hudson et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,536 B2 | 1/2004 | Vardi et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,919,690 B2 | 7/2005 | Siegfried et al. |
| 6,932,502 B2 | 8/2005 | Childers et al. |
| 6,935,768 B2 | 8/2005 | Löwe et al. |
| 7,004,173 B2 | 2/2006 | Sparks et al. |
| 7,153,315 B2 | 12/2006 | Miller |
| 7,169,165 B2 | 1/2007 | Belef et al. |
| 7,208,511 B2 | 4/2007 | Williams et al. |
| 7,318,831 B2 | 1/2008 | Alvarez et al. |
| 7,344,546 B2 | 3/2008 | Wulfman et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,629,829 B2 | 12/2009 | Lee |
| 7,699,790 B2 | 4/2010 | Simpson |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,771,444 B2 | 8/2010 | Patel et al. |
| 7,887,556 B2 | 2/2011 | Simpson et al. |
| 7,951,161 B2 | 5/2011 | Bonnette et al. |
| 7,959,634 B2 | 6/2011 | Sennett |
| 7,981,128 B2 | 7/2011 | To et al. |
| 8,007,506 B2 | 8/2011 | To et al. |
| 8,052,704 B2 | 11/2011 | Olson |
| 8,062,316 B2 | 11/2011 | Patel et al. |
| 8,070,762 B2 | 12/2011 | Escudero et al. |
| 8,109,951 B2 | 2/2012 | Maschke |
| 8,142,464 B2 | 3/2012 | Mitusina |
| 8,192,452 B2 | 6/2012 | Moberg |
| 8,208,990 B2 | 6/2012 | Maschke |
| 8,211,025 B2 | 7/2012 | Donaldson et al. |
| 8,236,016 B2 | 8/2012 | To et al. |
| 8,246,640 B2 | 8/2012 | Rosenthal et al. |
| 8,257,375 B2 | 9/2012 | Maschke |
| 8,275,201 B2 | 9/2012 | Rangwala et al. |
| 8,298,147 B2 | 10/2012 | Huennekens et al. |
| 8,328,829 B2 | 12/2012 | Olson |
| 8,361,094 B2 | 1/2013 | To et al. |
| 2001/0000041 A1* | 3/2001 | Selmon .............. A61B 17/3207 600/585 |
| 2001/0031784 A1 | 10/2001 | Petersen et al. |
| 2001/0031981 A1 | 10/2001 | Evans et al. |
| 2002/0019644 A1 | 2/2002 | Hastings et al. |
| 2002/0055732 A1 | 5/2002 | Wilson |
| 2002/0058904 A1 | 5/2002 | Boock et al. |
| 2002/0077642 A1 | 6/2002 | Patel et al. |
| 2002/0177800 A1 | 11/2002 | Bagaoisan et al. |
| 2003/0023263 A1 | 1/2003 | Krolik et al. |
| 2003/0039169 A1 | 2/2003 | Ehrfeld et al. |
| 2003/0120295 A1 | 6/2003 | Simpson et al. |
| 2003/0125757 A1 | 7/2003 | Patel et al. |
| 2003/0199747 A1 | 10/2003 | Michlitsch et al. |
| 2004/0049225 A1 | 3/2004 | Denison |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004594 A1 | 1/2005 | Nool et al. |
| 2005/0042239 A1 | 2/2005 | Lipiecki et al. |
| 2005/0090849 A1 | 4/2005 | Adams |
| 2006/0235334 A1 | 10/2006 | Corvi et al. |
| 2007/0049958 A1 | 3/2007 | Adams |
| 2007/0135886 A1 | 6/2007 | Maschke |
| 2007/0167824 A1 | 7/2007 | Lee et al. |
| 2007/0276419 A1 | 11/2007 | Rosenthal |
| 2008/0004645 A1 | 1/2008 | To et al. |
| 2008/0045986 A1 | 2/2008 | To et al. |
| 2008/0051812 A1 | 2/2008 | Schmitz et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216180 A1 | 8/2009 | Lee et al. |
| 2009/0275966 A1 | 11/2009 | Mitusina |
| 2009/0306689 A1 | 12/2009 | Welty et al. |
| 2010/0030216 A1 | 2/2010 | Arcenio |
| 2010/0130996 A1 | 5/2010 | Doud et al. |
| 2010/0312263 A1 | 12/2010 | Moberg et al. |
| 2011/0004107 A1 | 1/2011 | Rosenthal et al. |
| 2011/0130777 A1 | 6/2011 | Zhang et al. |
| 2011/0144673 A1 | 6/2011 | Zhang et al. |

FOREIGN PATENT DOCUMENTS

| | | |
|---|---|---|
| DE | 8900059 U1 | 5/1989 |
| DE | 9303531 U1 | 7/1994 |
| DE | 4444166 A1 | 6/1998 |
| DE | 29722136 U1 | 4/1999 |
| EP | 0107009 A2 | 5/1984 |
| EP | 0229620 A2 | 7/1987 |
| EP | 0330843 A1 | 9/1989 |
| EP | 0431752 A2 | 6/1991 |
| EP | 0514810 A1 | 11/1992 |
| EP | 1767159 A1 | 3/2007 |
| GB | 2093353 A | 9/1982 |
| GB | 2115829 A | 9/1983 |
| GB | 2210965 A | 6/1989 |
| JP | 4200459 A | 7/1992 |
| JP | 5042162 A | 2/1993 |
| JP | 5056984 A | 3/1993 |
| SU | 442795 A1 | 9/1974 |
| SU | 665908 A1 | 6/1979 |
| WO | 9746164 A1 | 12/1997 |
| WO | 9824372 A1 | 6/1998 |
| WO | 0030531 A1 | 6/2000 |
| WO | 0054735 A1 | 9/2000 |
| WO | 0062913 A1 | 10/2000 |
| WO | 0072955 A1 | 12/2000 |
| WO | 01/15609 A1 | 3/2001 |
| WO | 0115609 A1 | 3/2001 |
| WO | 0119444 A1 | 3/2001 |
| WO | 0130433 A1 | 5/2001 |

(56) References Cited

FOREIGN PATENT DOCUMENTS

| WO | 0245598 A2 | 6/2002 |
|---|---|---|
| WO | 2006058223 A2 | 6/2006 |

OTHER PUBLICATIONS

Brezinski et al., "Assessing Atherosclerotic Plaque Morphology: Comparison of Optical Coherence Tomography and High Frequency Intravascular Ultraound," Heart, 77:397-403 (1997).

Huang et al., "Optical Coherence Tomography," Science, 254:1178-1181 (1991).

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (2 pages).

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (2 pages).

Brezinski et al., "Optical Coherence Tomography for Optical Biopsy," Circulation, 93:1206-1213 (1996).

PCT International Search Report for PCT/US01/49220 dated Jun. 21, 2002, 1 pg.

PCT International Search Report and Written Opinion for PCT/US04/12601 dated Jun. 30, 2005, 4 pgs.

PCT International Search Report and Written Opinion for PCT/US04/12600 dated Jun. 13, 2008, 4 pgs.

PCT International Search Report and Written Opinion for PCT/US07/12008 dated Sep. 30, 2008, 4 pgs.

European Search Report regarding related application serial No. EP 04760156.2 dated Apr. 6, 2010, 3 pgs.

Extended European Search Report regarding related application serial No. EP 11151192.9 dated Apr. 11, 2011, 6 pgs.

Exam Report regarding related application serial No. EP 04760155.4 dated Jul. 19, 2011, 5 pgs.

Extended European Search Report regarding related application serial No. EP 12165347.1 dated Jun. 21, 2012, 7 pgs.

Extended European Search Report regarding related application serial No. EP 12165348.9 dated Jun. 21, 2012, 7 pgs.

European Search Report regarding related application serial No. EP 07795342.0 dated Sep. 3, 2012, 6 pgs.

European Search Report regarding related application serial No. EP 07809112.1 dated Apr. 23, 2013, 6 pgs.

Non-Final Office action for U.S. Appl. No. 12/431,210 dated Mar. 18, 2014, 7 pages.

Office Action for European Application No. 12 165 347.1, dated Jul. 14, 2014, 4 pages, Alexandria, Munich, Germany.

Non-Final Office for U.S. Appl. No. 13/551,123, dated Apr. 17, 2014, 9 pages, Alexandria, Virginia, United States.

Notice of Allowance for U.S. Appl. No. 13/536,497, dated May 15, 2014, 10 pages, Alexandria, Virginia, United States.

Office Action for U.S. Appl. No. 13/551,123, dated Aug. 4, 2014, 4 pages.

European Extended Search Report for Application No. 14194522.0, dated Mar. 25, 2015, 8 pages.

\* cited by examiner

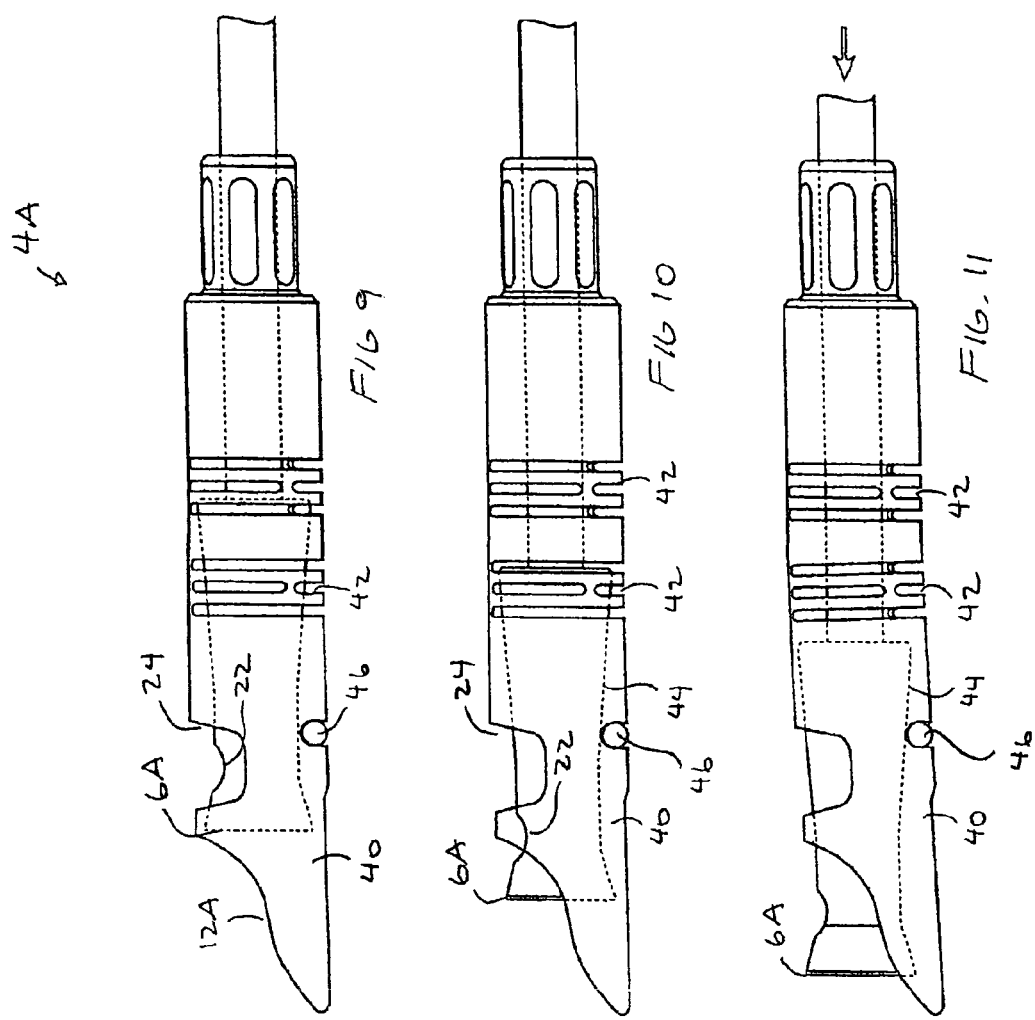

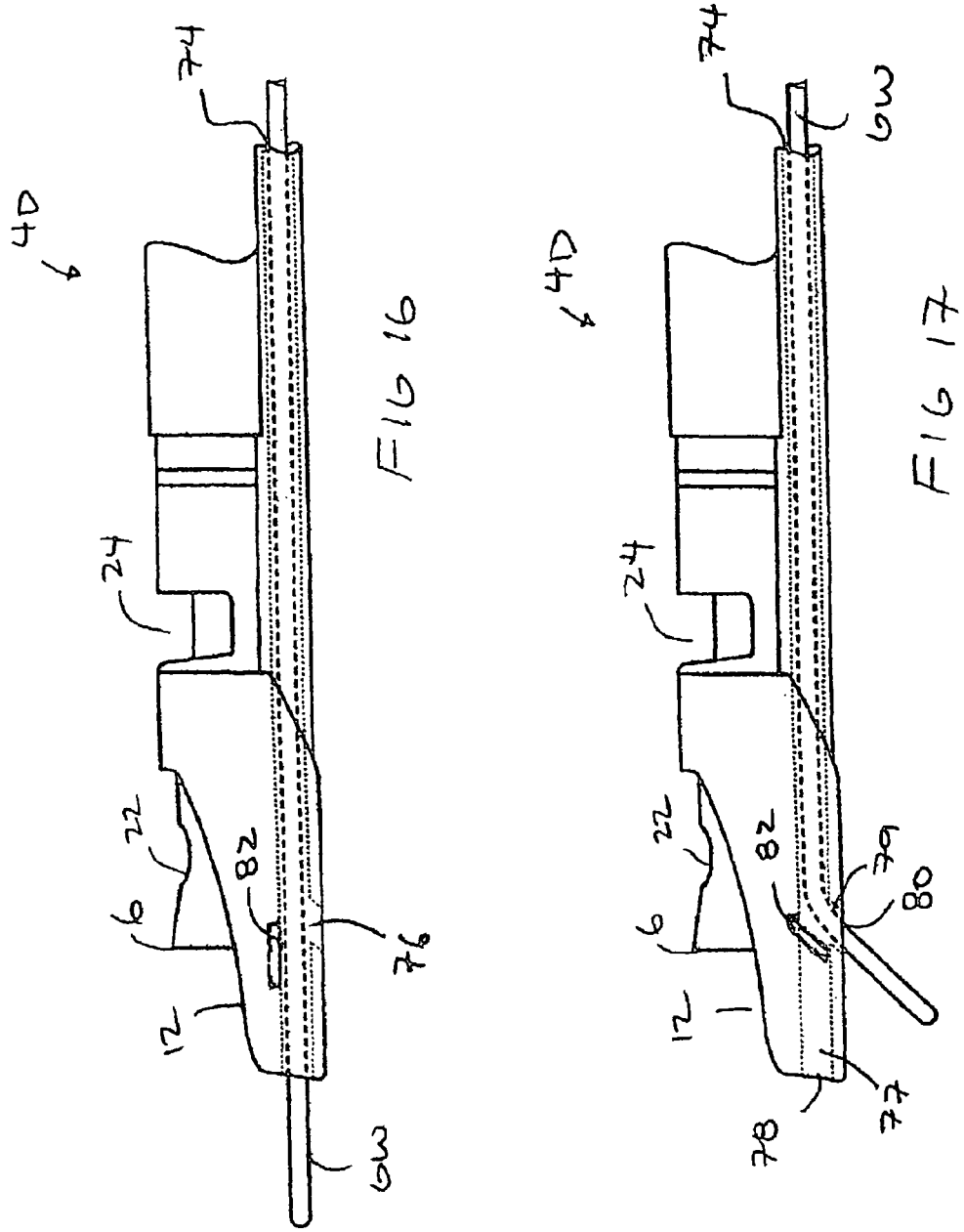

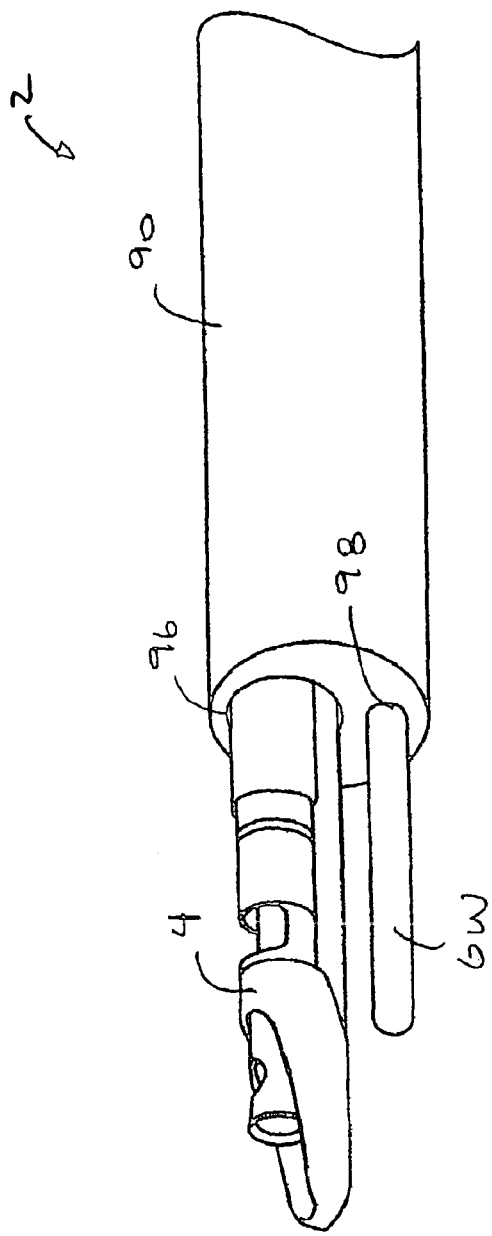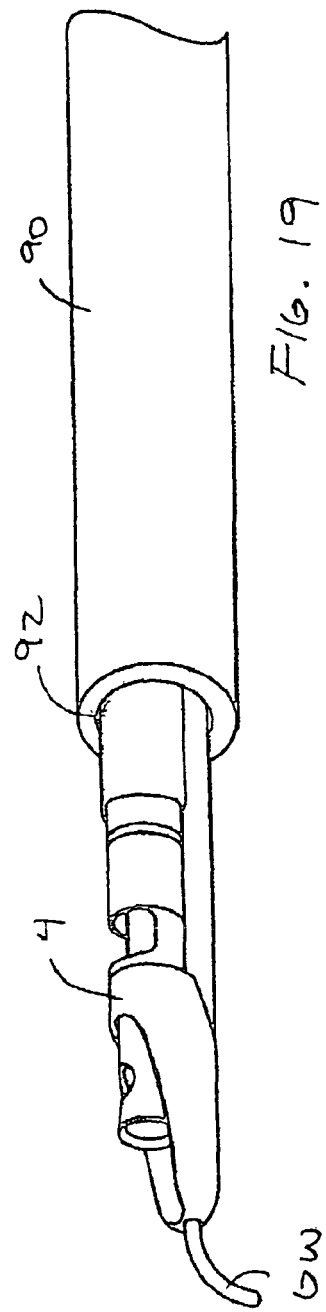

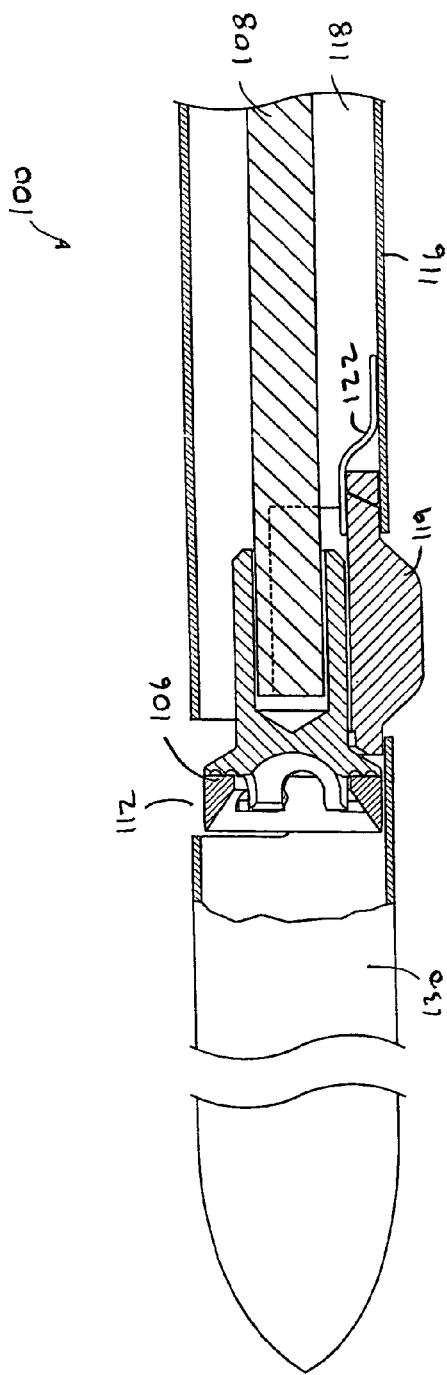
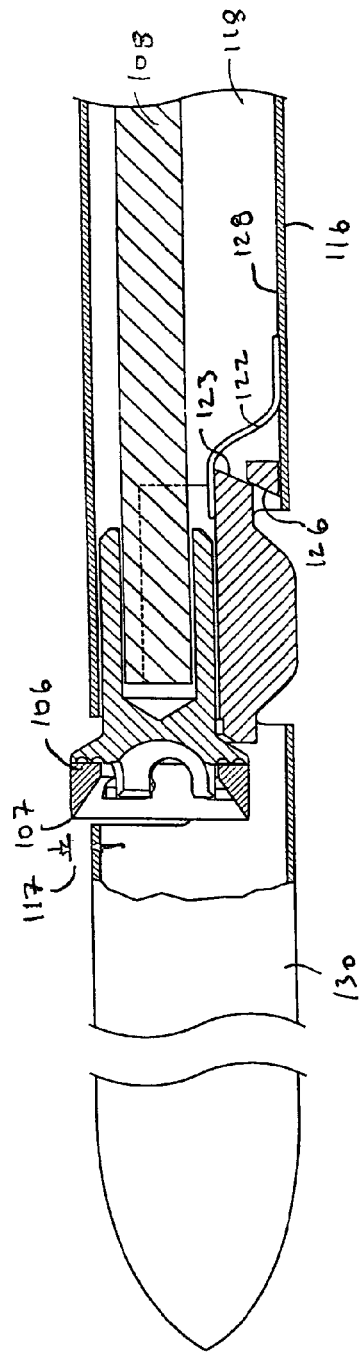
FIG. 22
FIG. 23

CATHETER INCLUDING CUTTING ELEMENT AND ENERGY EMITTING ELEMENT

CROSS-REFERENCE TO RELATED APPLICATIONS

The present application is a continuation application of U.S. patent Ser. No. 11/442,685, filed May 26, 2006, the entirety of which is incorporated by reference herein.

BACKGROUND OF THE INVENTION

The present invention is directed to devices and methods for cutting tissue. In a specific application, the present invention is directed to devices and methods for re-entering the true lumen from a subintimal space such as a dissection plane or so-called "false lumen."

Guidewires and other interventional devices are used to treat vessels and organs using endovascular approaches. A guidewire is typically guided through blood vessels to the treatment site and the device is then advanced over the guidewire. For example, angioplasty and stenting are generally accomplished by first introducing a guidewire to the desired site and then advancing the angioplasty or stent catheter over the guidewire.

When attempting to advance a guidewire or other interventional device through a highly stenosed region or chronic total occlusion (CTO), the guidewire or device may inadvertently enter into the wall of the vessel to create a sub-intimal space. Once in a sub-intimal space, it can be difficult to re-enter the vessel true lumen. Devices for reentering a vessel true lumen from a subintimal location are described in WO 02/45598 which is hereby incorporated by reference.

BRIEF SUMMARY OF THE INVENTION

In one aspect of the present invention, a catheter is provided which has a rotating active element and a rotating energy emitter. The active element is mounted to a shaft. The energy emitter may be mounted to another shaft. The elements rotate independently which may provide advantages over devices which couple the energy emitter and cutting element (or other active element) together. A problem with devices which couple the energy emitter to another rotating element, such as a cutting element, is that rotation of the energy emitting element may be disrupted by resistance met by the cutting element during rotation. Disruption in rotation of the energy emitting element can negatively impact the ability to gather useful information from the energy received.

BRIEF DESCRIPTION OF THE DRAWINGS

FIG. 9 shows another reentry device with the cutting element in a stored position.

FIG. 10 shows the reentry device of FIG. 9 with the cutting element in a cutting position and the distal portion bent.

FIG. 11 shows the reentry device of FIGS. 9 and 10 with the cutting element advanced to another cutting position which exposes even more of the cutting element and also bends the distal tip further.

FIG. 16 shows the reentry device of FIG. 6 having a junction leading to two separate guidewire outlets with the guidewire positioned in the first outlet during advancement of the device over the guidewire.

FIG. 17 shows the reentry device of FIG. 16 with the guidewire extending through the second outlet for directing the guidewire into the true lumen.

FIG. 18 shows a catheter having a lumen for receiving a guidewire and another lumen which receives the reentry device.

FIG. 19 shows another catheter having a single lumen through which the guidewire and reentry device pass.

FIG. 22 is a cross-sectional view of the device of FIGS. 20 and 21.

FIG. 23 is a cross-sectional view of the device of FIGS. 20 and 21 with the sizer moved inward.

DETAILED DESCRIPTION OF THE INVENTION

Figure 1:
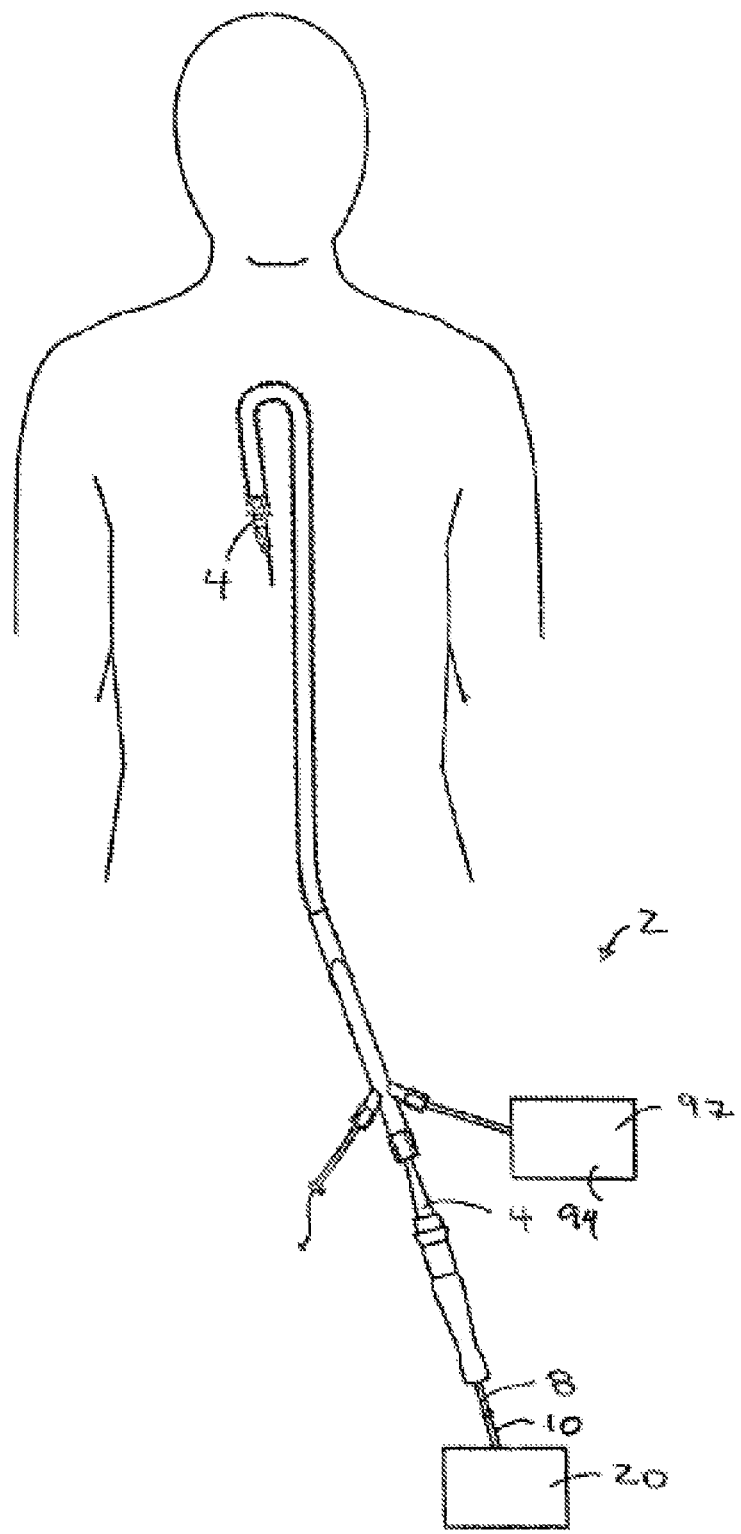
FIG. 1 shows a view of the system of the present invention.

Referring to FIGS. 1-8, a system 2 and device 4 for reentering a true lumen from a subintimal space, dissection plane or so-called false lumen is shown. The device 4 includes a cutting element 6 coupled to a torque transmitting element 8, such as a wire 10, which rotates the cutting element 6. The device 4 has an opening 12 at a distal end 14 with the cutting element 6 movable between a stored position (FIG. 6) and a cutting position (FIGS. 7 and 8) which exposes the cutting element 6. The cutting element 6 may be any suitable cutting element 6 such as the cutting element 6 described in patents incorporated by reference above. The cutting element 6 has a circular cutting edge which has a diameter of about 1 mm although any suitable size may be used depending upon the particular application. The cutting element 6 may also be any other type of cutter such as a laser, ultrasound, RF or other type of cutter without departing from various aspects of the present invention.

The device 4 has a flexible body 16 to navigate through blood vessels or other body lumens to a target location. The body 16 may be made of any suitable material as is known in the art such as Pebax. The torque transmitting element 8 extends through a lumen 18 in the body 16. The body 16 may have more lumens for various reasons such as introduction of fluids, such as contrast, or for delivery of another device 4 such as a guidewire or interventional device. The torque transmitting element 8 is coupled to a driver 20 which rotates the torque transmitting element 8 at a variable or fixed speed.

The device 4 may also have an energy emitting element 22, such as an ultrasound element 25, which emits (and may receive) energy to determine the location of the true lumen as explained below. The energy emitting element 22 is coupled to the cutting element 6 so that the energy emitting element 22 and cutting element 6 are rotated together. The cutting element 6 is in the stored position when locating the true lumen so that the cutting element 6 is not exposed and will not cut or damage tissue. The energy emitting element 22 is positioned adjacent a window 24 which may be a side opening 26 or may simply be a portion of the sidewall which transmits a sufficient amount of the energy therethrough. Any suitable energy emitting element 22 may be used such as the ultrasound emitting element available from Boston Scientific and is marketed under the name Atlantis™. The cutting element 6 may be mounted to a collar which is then mounted to an ultrasound element holder 28 or the cutting element 6 may be integrally formed with the ultrasound element holder 28.

The device 4 has an atraumatic tip 34 which is relatively flexible to prevent damaging tissue. The tip 34 may be a separate piece laminated or glued to the body 16. The tip 34 is preferably made out of a relatively soft, flexible material, such as tecothane, and may be used for blunt dissection as necessary. A reinforcing element 36 is encapsulated in the tip 34 to help the tip 34 maintain its general shape. The tip 34 may also have one or more guidewire lumens 38 or any of the guidewire features described herein.

Figure 7:
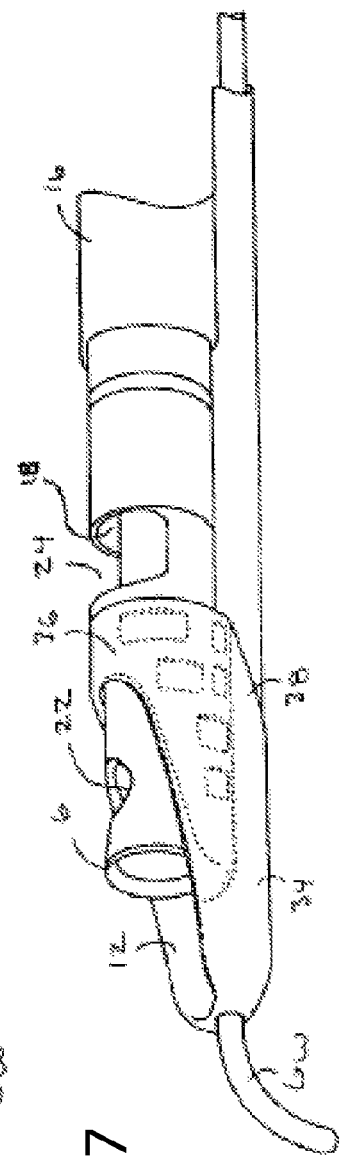
FIG. 7 shows the reentry device with the cutting element in a cutting position.
Figure 8:
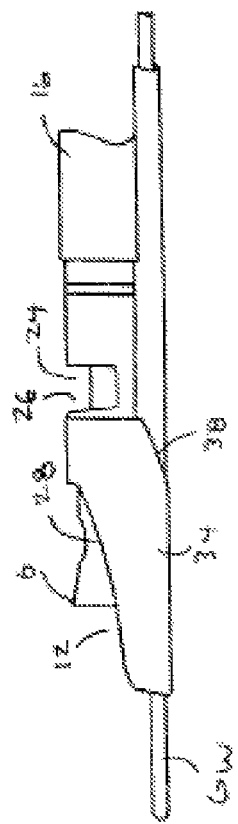
FIG. 8 is a side view of the reentry device of FIG. 7.

The opening 12 in the distal portion may be designed to expose over 180 degrees of the cutting element 6 and may even expose 220 degrees or even 270 degrees of the cutting element 6 as defined by the axis of rotation. This provides advantages over WO 02/45598 which does not expose much of the cutting element 6 and requires invagination of the tissue within the opening to cut tissue. In another aspect of the invention, the cutting element 6 may be gradually exposed. For example, the cutting element 6 may be gradually exposed from 180-220 degrees or even 200-270 degrees. As explained below, this feature provides the user with the ability to change the amount of cutter 6 that is exposed depending upon the tissue thickness between the subintimal location and true lumen. The term opening 12 and amount of exposure of the cutting element 6 are defined by the outer bounds of the opening 12 and the axis of rotation. Referring to FIGS. 7 and 8, the cutting element 6 is exposed relative to the outer bounds of the opening 12 due to the relatively open distal end.

Referring to FIGS. 9-11, another device 4A for reentering a true lumen from a subintimal location is shown wherein the same or similar reference numbers refer to the same or similar structure. The device 4A also has an opening 12A at the distal end to expose the cutting element 6A. FIG. 9 shows the cutting element 6A in a stored position, FIG. 10 shows the cutting element 6A in a first cutting position and FIG. 11 shows the cutting element 6A in a second cutting position which further exposes the element 6A. The device 4A also has the window 24 through which the energy emitting element 22, such as the ultrasound element, may emit energy when the cutting element 6A is in the stored position.

A distal portion 40 of the body can bend or articulate to further expose the cutting element 6A and to move the cutting element 6A toward true lumen. The body has slots 42 formed therein to increase the flexibility of the distal portion 40. The cutting element 6A has a surface 44 which engages a lip 46 on the body. As the cutting element 6A is advanced, the interaction between the surface 44 and lip 46 causes the distal portion 40 to deflect. Bending the distal portion 40 can be helpful in moving the cutting element 6A toward the tissue and may also expose more of the cutting element 6A. As also explained below, the tip 40 may also be bent to direct the device 4A itself or a guidewire into the true lumen. The cutting element 6A may also be gradually exposed as the cutting element 6A moves distally and may be gradually exposed in the same manner described above.

Figure 12:
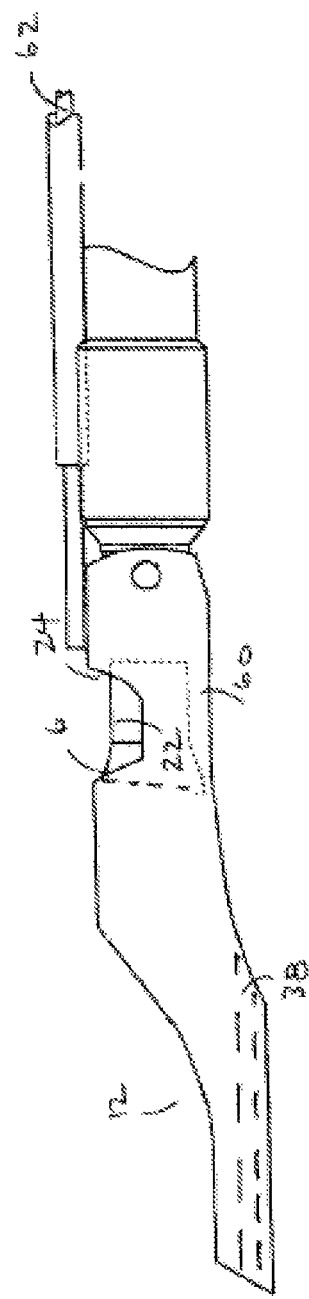
FIG. 12 shows another reentry device which has a bendable distal portion.
Figure 13:
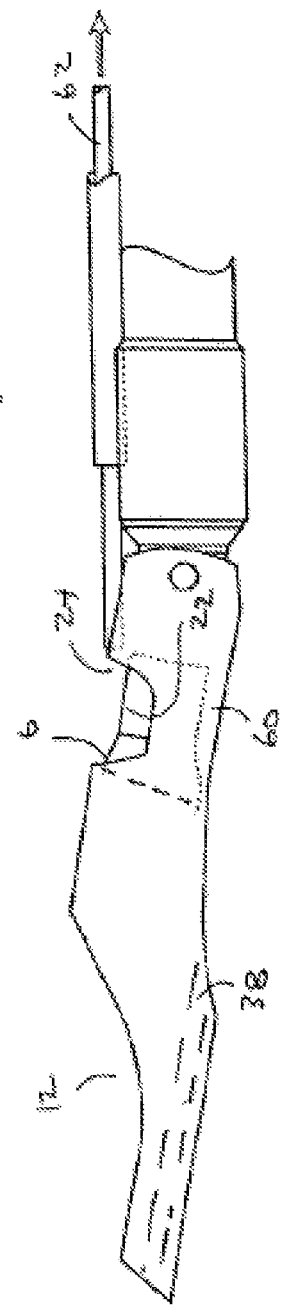
FIG. 13 shows the reentry device of FIG. 12 with the distal portion bent.

Referring to FIGS. 12 and 13, another reentry device 4B is shown which has a distal portion or tip 60 which bends or articulates. The tip 60 may be articulated and actuated in any suitable manner. For example, the tip 60 may be bent upon longitudinal movement of the cutting element 6 (as shown above) or a separate actuator, such as a pull wire 62, may be used. As can be appreciated from FIG. 13, the tip 60 is bent or articulated to move the cutting element 6 toward the true lumen and to expose more of the cutting element 6. The device 4B may also be bent to direct the device 4B itself or another device or guidewire through the guidewire lumen 38 to the access path into the true lumen as described further below.

Figure 14:
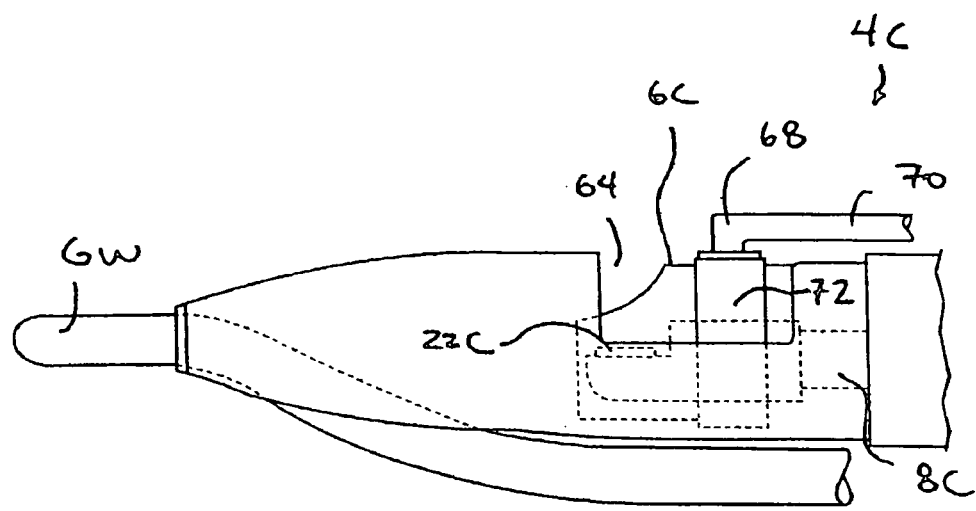
FIG. 14 shows still another reentry device with a cutting element which may be tilted.
Figure 15:
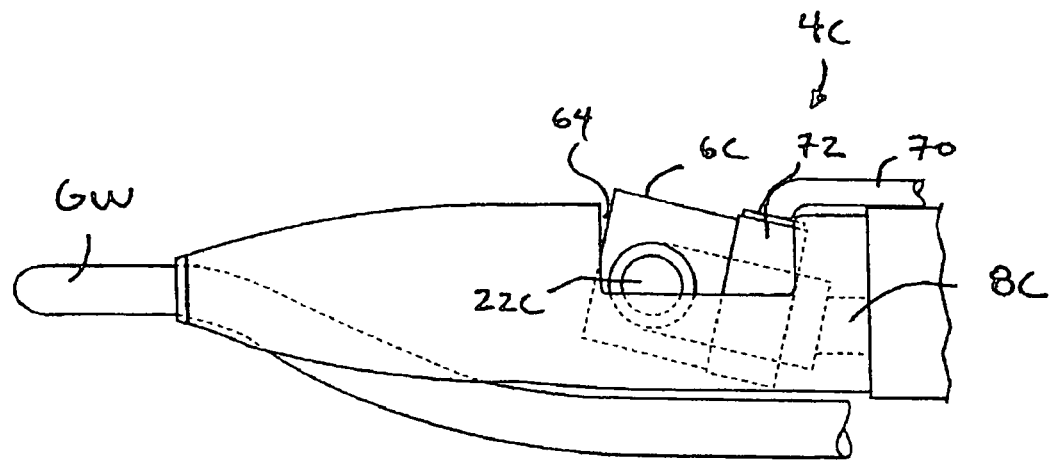
FIG. 15 shows the reentry device of FIG. 14 with the cutting element tilted to expose more of the cutting element and to move the cutting element through the opening in the body of the device.

Referring to FIGS. 14 and 15, still another device 4C for cutting tissue is shown wherein the same or similar numbers refer to the same or similar structure. The device 4C includes a cutting element 6C, an energy emitting element 22C and a torque transmitter 8C for rotating the elements. The device 4C has an opening 64 along one side. The cutting element 6C is contained within the opening 64 in the stored position of FIG. 14 and extends out of the opening 64 in the cutting position of FIG. 15. The cutting element 6C is moved out of the window 24 using an actuator 68, such as a wire 70, which tilts a bearing 72 supporting the shaft of the rotatable cutting element 6C. Of course, any other suitable structure may be used to move the cutting element 6C outside the opening 64 such as those described in U.S. Pat. No. 6,447,525 which is hereby incorporated by reference. Furthermore, the cutting element 6C may be moved out of the opening 64 by bending the distal portion or tip as described herein.

Figure 2:
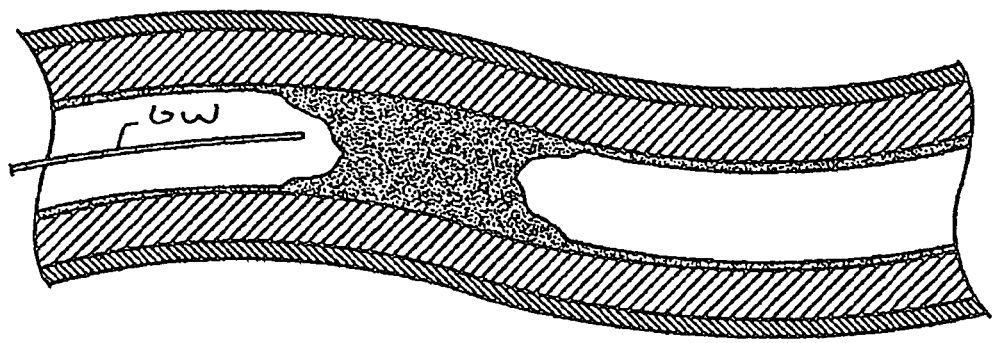
FIG. 2 shows a guidewire positioned proximate to a total occlusion.
Figure 3:
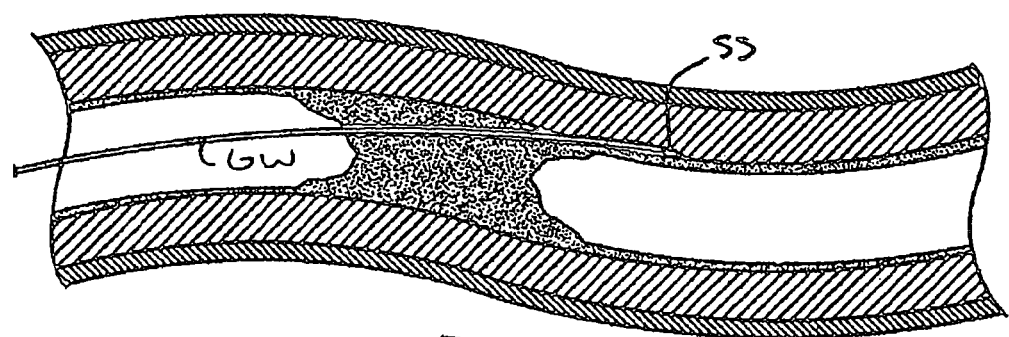
FIG. 3 shows a subintimal space created adjacent a true lumen by the guidewire.
Figure 4:
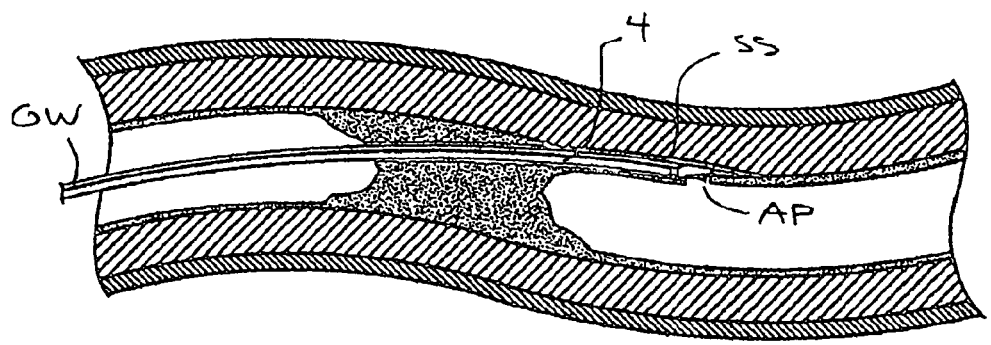
FIG. 4 shows a reentry device of the present invention advanced over the guidewire to the subintimal space.
Figure 5:
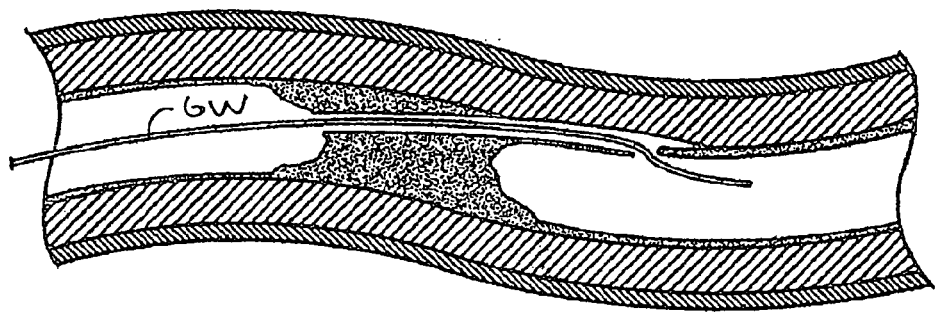
FIG. 5 shows a guidewire positioned in the true lumen.
Figure 6:
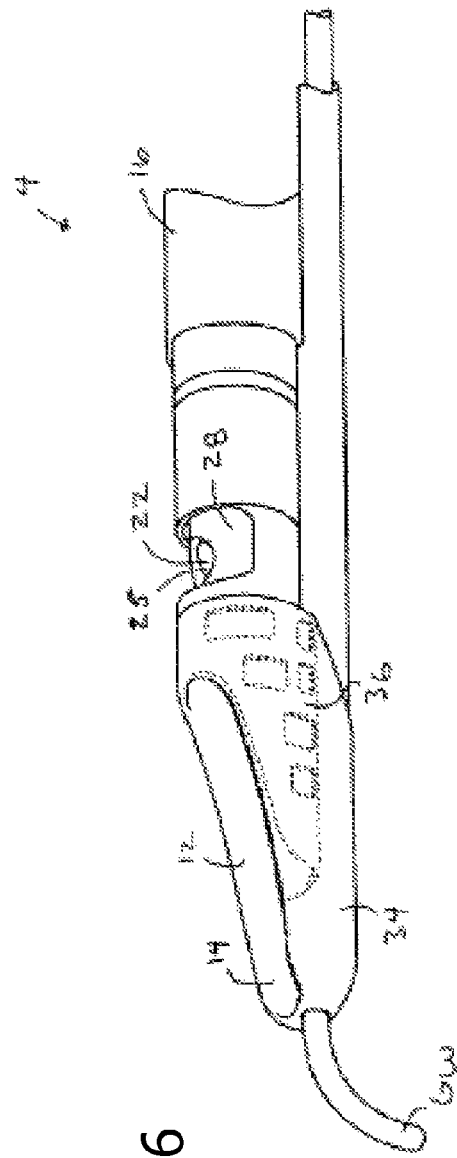
FIG. 6 shows the reentry device with the cutting element in a stored position.

Use of the devices 4, 4A-C is now described with reference to the device 4 although it is understood that any of the devices 4, 4A-C may be used. As mentioned above, the device 4 may be used to perform any suitable procedure to cut from one location to another in the body such as a procedure to reenter a true lumen. The device 4 is initially advanced to a position within a subintimal space SS. As described above, the subintimal space SS may be inadvertently created during an endovascular procedure with a guidewire GW or other device creating the subintimal space SS as shown in FIGS. 2 and 3. The device 4 may be introduced over the same guidewire GW or device which created the subintimal space SS as shown in FIGS. 4 and 5. Of course, the device 4 may also be advanced over the guidewire GW to a position proximate to the subintimal space SS after which the device 4 is then advanced by itself into the subintimal space SS.

After the device 4 is positioned at the appropriate location in the subintimal space SS, the energy emitting element 22 is used to determine the location of the true lumen. When using the ultrasound element 28, for example, the ultrasound element 28 is rotated while emitting ultrasound energy and the energy emitted through the window 24 and reflected back through the window 24 is processed as is known in the art. The entire device 4 is rotated within the subintimal space SS to orient the window 24 until the true lumen is located. The angular orientation of the device 4 is then maintained so that the opening 12 and window 24 are directed toward the true lumen.

The cutting element 6 is then moved to the cutting position to expose the cutting element 6. The cutting element 6 may be rotated with the driver 20 during this time so that cutting is initiated as the cutting element 6 is exposed. In another aspect of the invention, the entire device 4 itself may be moved through the subintimal space to cut tissue. This provides advantages over the method of WO 02/45598 which requires invagination of tissue through a window to attempt a cut at one location. If the tissue does not invaginate sufficiently into the window, such as when the tissue is too thick, the device of WO 02/45598 will not be able to cut completely through the tissue to create the access path to the true lumen. The user must then move the device and again attempt to invaginate enough tissue to cut an access path. The present invention provides the ability to move the entire device 4 through the subintimal space to create the access path rather than attempting a cut at a single discrete location as in WO 02/45598. Of course, the device 4 may also be used by moving only the cutting element 6 rather than the entire device 4 without departing from the invention.

The cutting element 6 may also be exposed to varying degrees, as described above, until enough of the cutting element 6 is exposed to cut through to the true lumen. For example, the user may choose to expose half of the cutting element 6 and attempt to create an access path to the true lumen. If an access path is not created, the user may then choose to expose more of the cutting element 6 and again attempt to create an access path. This procedure can be repeated until the access path is formed to the true lumen. The device 4A, 4B may be also have a distal tip or portion 40, 60 which bends to move the cutting element 6 toward the tissue and/or expose more of the cutting element 6 during cutting.

After successfully creating the access path into the true lumen, the device 4 itself or part thereof may be directed toward or through the access path. Referring to FIGS. 9-13, for example, the distal portion or tip 40, 60 may be bent to help direct the device 4A, 4B itself or the guidewire GW through the access path.

Referring to FIGS. 16 and 17, another device 4D, similar to device 4, is shown which has a guidewire lumen 74 having a junction 76 so the guidewire can be directed through either a first lumen 77 having a first outlet 78 or a second lumen 79 having a second outlet 80. The first outlet 78 directs the guidewire substantially longitudinally for advancing the device 4D over the guidewire to the target area in a conventional manner. The second outlet 80 directs the guidewire at an angle relative to the longitudinal axis, such as 30-75 degrees, to direct the guidewire through the access path into the true lumen.

The junction 76 may include a feature which directs the guidewire into the second outlet 80. Referring to FIG. 17, for example, the junction 76 may include a flap or stop 82 which closes and prevents or inhibits the guidewire from passing through the first outlet 78 after the guidewire has been withdrawn proximal to the junction 76. When the guidewire is advanced again as shown in FIG. 17, the guidewire passes through the second outlet 80 due to the stop 82. The device 4 and/or guidewire GW are then manipulated to direct the guidewire GW through the access path. Although the stop 82 may be provided, the junction 76 may also simply be a relatively open junction 76 with the user manipulating and rotating the guidewire GW to direct the guidewire GW through the desired outlet 78, 80. The device is rotated about 180 degrees after creating the access path to direct the GW through outlet 80 and into the true lumen.

Referring to FIGS. 18 and 19, the system 2 may also include a sheath or catheter 90 which is advanced proximal to the treatment site. The sheath 90 may help provide better control of the guidewire GW and devices 4 of the present invention during manipulation in the subintimal space. The sheath 90 may also used to deliver contrast solution to the treatment site from a source of contrast 97 (see FIG. 1) or may be coupled to a pressure sensor 94. The pressure sensor 94 may be part of the contrast delivery system 97 or may be a separate component. Deliver of contrast and/or pressure monitoring may be used to determine when the access path has been created.

The sheath 90 may include only one lumen 92 with fluid delivery and pressure sensing being accomplished in the annular space between the device and sheath as shown in FIG. 19. The sheath 90 may also have first and second lumens 96, 98 for separate delivery of the device 4 and guidewire GW. As mentioned above, the devices 4 of the present invention may be advanced over the same guidewire or device that created the subintimal space or may be advanced over another guidewire or even through the sheath 90 by itself.

After accessing the true lumen, another interventional device may be introduced into the true lumen for the intended therapy or procedure. For example, a stent catheter, angioplasty catheter, or atherectomy device may be used to treat the occlusion. The present invention has been described for reentering a true lumen from a subintimal space but, of course, may be used for other purposes to gain access from one space to another anywhere within the body.

Referring to FIGS. 20-23, another device 100 for cutting tissue is shown wherein the same or similar reference numbers refer to the same or similar structure. The device 100 includes an elongate body 116 and a cutting element 106 coupled to a drive element 108 which is rotated to drive the cutting element 106. The drive element 108 extends through a lumen 118 in the body 116 and is driven by a driver (not shown) at the proximal end. The cutting element 106 may be any suitable cutting element 106 including those described in the applications incorporated herein. The cutting element 106 has an essentially circular cutting surface 107 along the leading edge of the cutting element 106.

Figure 20:
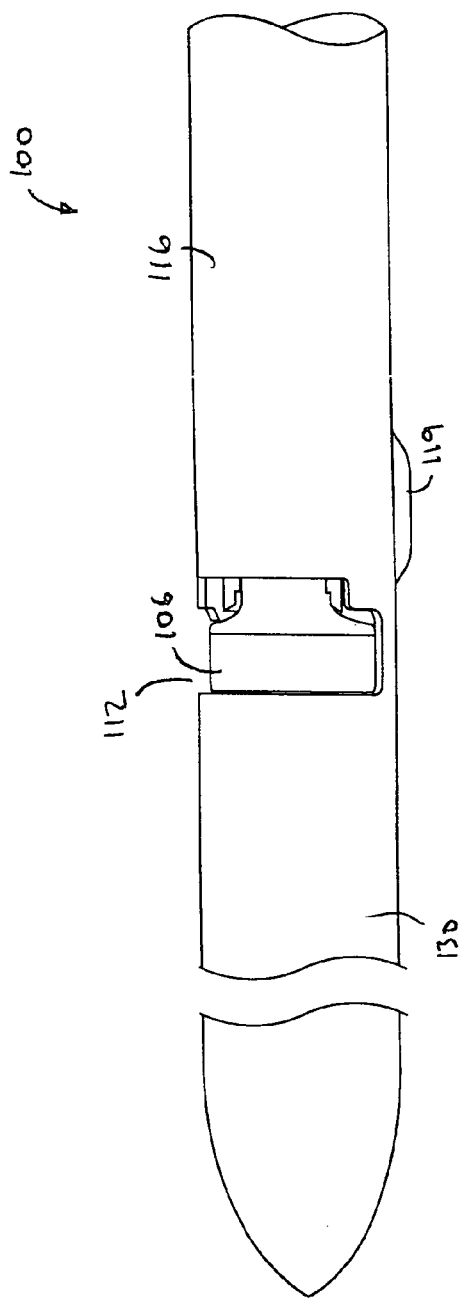
FIG. 20 shows an external view of another device for cutting tissue having a sizer.
Figure 21:
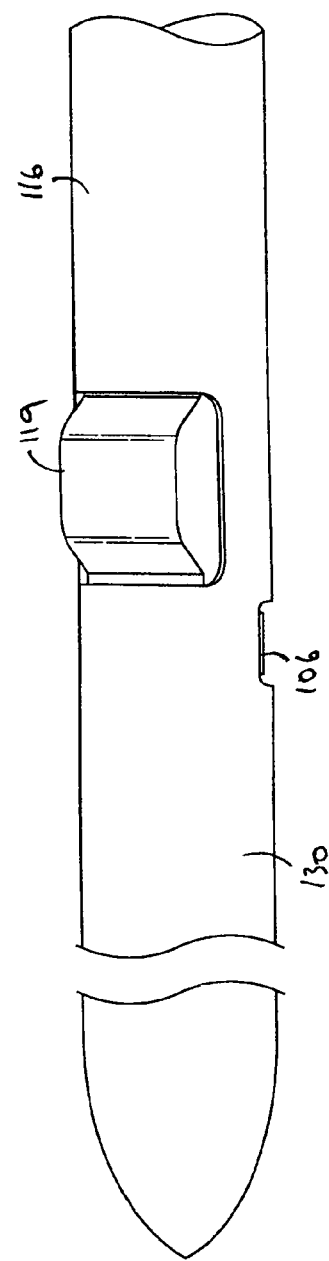
FIG. 21 shows another external view of the device of FIG. 20.

The body 116 has an opening 112 therein and the tissue cutter 106 is movable from the stored position of FIGS. 20 and 22 to the cutting position of FIG. 23. When moved to the cutting position of FIG. 23, part of the tissue cutting element 116 becomes exposed relative to opening 112. The opening 112 may be a side opening as shown in FIGS. 20-23 or may be a distal opening as shown in other devices described herein such as the devices of FIGS. 1-19. The tissue cutting element 106 moves relative to the body 116 so that a cutting height 117 of the tissue cutting element 106 changes as the position of the cutting element changes relative to the body 116. The cutting height 117 is defined by a maximum distance from the cutting surface 107 to an outer surface 109 of the body 116.

The device 100 has a sizer 119 coupled to the body 116 which automatically adjusts the cutting height 117 based on vessel size. The sizer 119 is naturally biased to an outer position of FIG. 22 by a spring 122 which defines a maximum width of the device along the sizer 119. The sizer 119 is moved inward from the position of FIG. 22 when contact with the vessel wall overcomes the force biasing the sizer 119 outward. In simplistic terms, the sizer 119 is essentially moved inward by the vessel wall when the vessel size is smaller than the width of the device 100. Thus, the sizer 119 moves between the positions of FIGS. 22 and 23 as the diameter of the vessel varies within a given range. When the vessel diameter is larger than the diameter of the device 100, the tissue cutting element 106 will remain in the stored position of FIG. 22. Stated another way, the sizer 119 is coupled to the tissue cutting element 106 so that an outward force is applied to the tissue cutting element 106 when the sizer 119 moves inward. The outward force on the tissue cutting element 106 being directed away from the body 116.

The sizer 119 is coupled to the tissue cutting element 106 so that the amount of exposure of the cutting element, such as the cutter height 117, changes when the vessel diameter changes. In the embodiment of FIG. 16, the exposure of the tissue cutting element 106 is increased when the vessel diameter decreases so that a deeper cut is made in smaller vessels. A deeper cut may be desired when removing tissue in smaller vessels to increase the flow of blood through the vessel. The user may still move the tissue cutting element 106 to the cutting position of FIG. 23 by pulling on the drive element 108 so that a contact surface 123 on the sizer 119 engages a ramp 126 on an inner wall 128 of the body 116 to move the cutting element 106 to the position of FIG. 23.

The tissue cutting device 100 may be used to cut tissue for any purpose. Furthermore, the device 100 has been described in connection with cutting tissue in blood vessels but may be used for any other purpose in the vasculature. The tissue may be cut and left within the body or may be removed in any suitable manner. For example, the device 100 may include a tissue collection chamber 130 coupled to the body 116 distal to the cutting element 106. The tissue cutting element 106 cuts tissue and directs the tissue into the collection chamber 130. The tissue cut by the tissue cutting element 106 is parted off from the surrounding tissue by moving the cutting element 106 back to the stored position.

Figure 24:
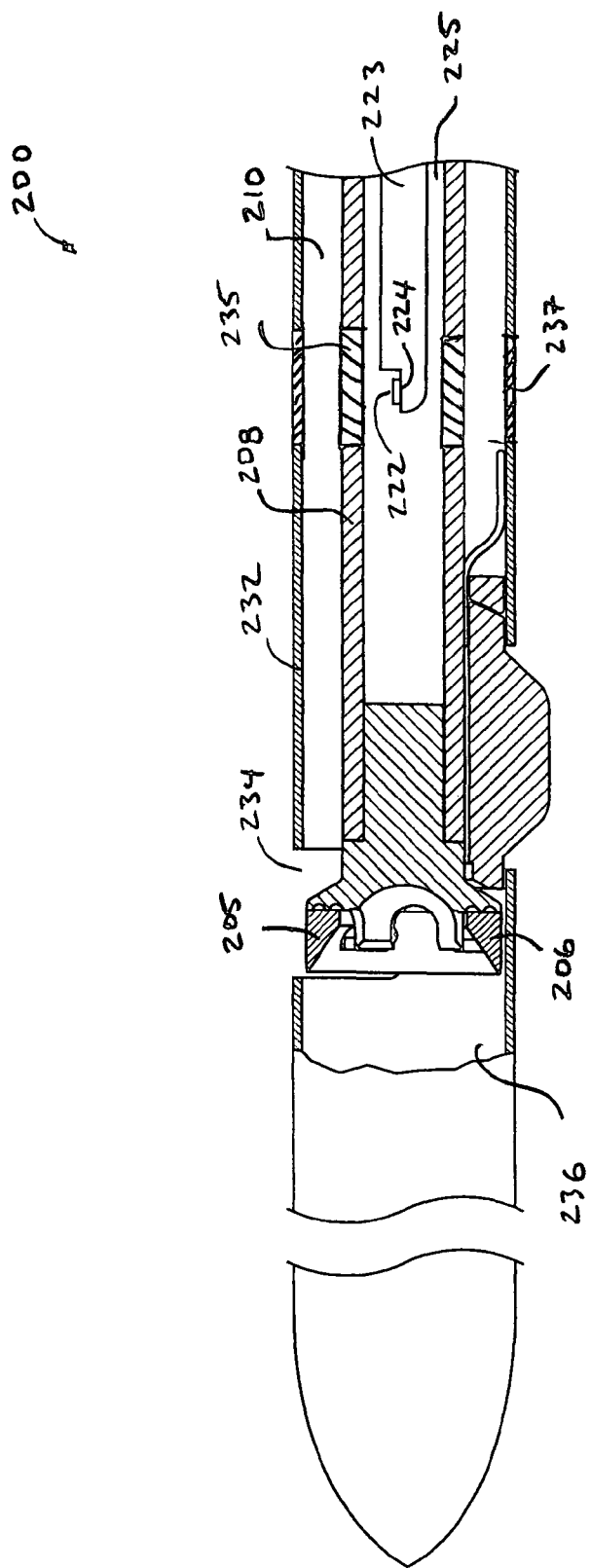
FIG. 24 shows another catheter for cutting tissue.

Referring to FIG. 24, another catheter 200 is shown which is similar to the device 100 described above and description of the device 100 is incorporated here. The catheter 200 has an elongate body 232 and an active element 205, such as a tissue cutting element 206, which is mounted to a drive shaft 208. The drive shaft 208 is positioned in a lumen 210 in the body 232. The body 232 has an opening 234 and the cutting element 206 is movable relative to the opening 234 between the stored position of FIG. 24 and a cutting position in which the cutting element 206 extends out of the opening 234 (not shown).

An energy emitting element 222, such as an ultrasound element 224, is mounted to a shaft 223 positioned in a lumen 225 in the drive shaft 208 of the active element 205. The energy emitting element 222 emits energy toward tissue which is reflected back from the tissue to the catheter 200 and measured by the catheter 200 to provide information about the vasculature. The energy reflected back to the catheter 200 may be received by the energy emitting element 222 itself, such as when using the ultrasound element 224, or may be received by another part of the catheter 200 other than the emitter 222. The energy which is received back at the catheter 200 is then processed as is known in the art to provide the user with information such as an image of the vessel.

The drive shaft 208 and the body 232 each have a part 235, 237 adjacent to the emitter 222 which permits energy to pass therethrough. Energy reflected back at the catheter 200 from the tissue may also pass back through the parts 235, 237 of the body 232 and shaft 208 to be received by the emitter 222 or another part of the catheter 200. Of course, the catheter 200 may also have an open window through which energy is emitted rather than directing energy through parts of the body 232 and/or shaft 208.

Figure 25:
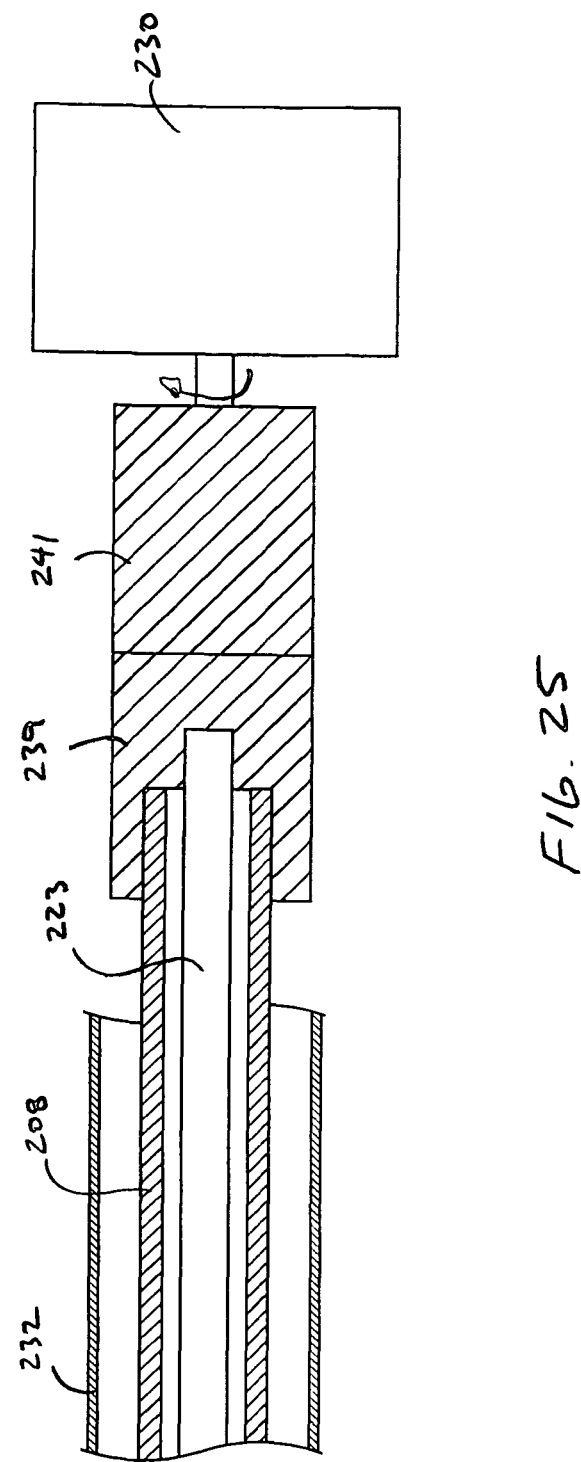
FIG. 25 shows a proximal end of the catheter of FIG. 24.

Referring now to FIGS. 24 and 25, the drive shafts 208, 223 of the energy emitting element 222 and the active element 205 may both be coupled to and driven by a single rotating driver 230. Although both rotating elements 205, 222 may be driven by the same driver, the elements 205, 222 may rotate somewhat independently which may provide advantages over devices which couple the energy emitter and cutting element (or other active element) together. A problem with devices which couple the energy emitter to another rotating element, such as a cutting element, is that rotation of the energy emitting element may be disrupted by resistance met by the cutting element during rotation. Disruption in rotation of the energy emitting element can negatively impact the ability to gather useful information from the energy received. Separating the energy emitting element 222 from the cutting element 206 isolates the energy emitting element 222 from potential disruptions caused by disruptions in rotation of the cutting element 206. To this end, the two drive shafts 208, 223 may be unattached to one another for a length of at least 10 cm or at least 20 cm from the energy emitting element. The drive shafts 208, 223 are free of attachments to one another until they reach a proximal hub 239 which couples the two shafts 208, 223 together as shown in the schematic representation of FIG. 25. The hub 239 is coupled to a connector 241 on the driver 230 so that the proximal end of the shafts 208, 223 essentially rotate together. Although the proximal ends of the shafts 208, 223 may be coupled together, the energy emitting element 222 and cutting element 205 at the distal ends of the shafts 208, 223 are somewhat free to rotate relative to one another since each shaft 208, 223 acts like a torsion spring which stores and releases energy as necessary. For example, the cutting element 206 may encounter resistance which slows or stops rotation. The shaft 208 will act like a torsion spring which permits the cutting element 206 to lag behind rotation of the energy emitting element 222. Of course, the two shafts 208, 223 may be free to rotate relative to one another along their entire length without departing from numerous aspects of the invention.

Although the catheter 200 has been described in connection with cutting tissue, the catheter 200 may use any other suitable active element which is rotated such as an ablating element, a diagnostic tool, or a drug delivery element. The tissue which has been cut may be left in the body or removed in any suitable manner. For example, the catheter 200 may also have a tissue collection element 236 positioned distal to the cutting element 206. The cutting element 206 cuts tissue and directs the tissue through the opening 234 in the body 232 and into the tissue collection element 230 as the catheter 200 is advanced.

The present invention has been described in connection with the preferred embodiments, however, it is understood that numerous alternatives and modifications can be made within the scope of the present invention as defined by the claims.

What is claimed is:

1. A catheter for removing tissue from a body lumen and for providing information relating to the body lumen, the catheter comprising:

an elongate catheter body having a length and opposite proximal and distal end portions;

a first drive shaft positioned in the catheter body, the first drive shaft being rotatable relative to the catheter body;

a tissue cutting element adjacent the distal end portion of the catheter body and configured to rotate relative to the catheter body, the tissue cutting element being mounted to the first drive shaft to impart rotation to the tissue cutting element;

a second drive shaft positioned in the catheter body, the second drive shaft being rotatable relative to the catheter body; and an energy emitting element adjacent the distal end portion of the catheter body and configured to rotate relative to the catheter body, the energy emitting element being mounted to the second drive shaft to impart rotation to the energy emitting element, the energy emitting element being rotatable independently of the tissue cutting element at the distal end portion, wherein the energy emitting element is positioned in the catheter body at a location that is proximal to the tissue cutting element to define a longitudinal distance between the energy emitting element and the tissue-cutting element, wherein the energy emitting element is non-movable and fixed relative to the length of the catheter body to inhibit movement of the energy emitting element along the length of the catheter body, wherein the longitudinal distance between the energy emitting element and the tissue cutting element is fixed and non-adjustable to inhibit adjustment of the longitudinal distance between the energy emitting element and the tissue cutting element, wherein proximal ends of the respective first and second drive shafts are rotatably coupled together so that the proximal ends of the first and second drive shafts rotate together.

2. The catheter set forth in claim 1, wherein the catheter body includes a part adjacent to the energy emitting element that permits energy emitted from the energy emitting element to pass therethrough to the body lumen.

3. The catheter set forth in claim 2, wherein the energy emitting element is configured to receive emitted energy that is reflected back from the body lumen.

4. The catheter set forth in claim 2, wherein the first drive shaft defines a lumen, the energy emitting element being positioned in the lumen of the first drive shaft, wherein the first drive shaft includes a part adjacent to the energy emitting element that permits energy emitted from the energy emitting element to pass therethrough.

5. The catheter set forth in claim 1, wherein the catheter body defines a side opening extending generally transversely into the catheter body, wherein the tissue cutting element is movable relative to the side opening between a stored position, in which the tissue cutting element is received in the catheter body, and a cutting position, in which the tissue cutting element extends out of the side opening.

6. The catheter set forth in claim 5, wherein the tissue cutting element includes a circular cutting surface.

7. The catheter set forth in claim 1, further comprising at least one driver configured for operative connection to said first and second drive shafts for driving rotation of said first and second drive shafts.

8. The catheter set forth in claim 1, wherein the energy emitting element comprises an ultrasound element.

9. The catheter set forth in claim 8, wherein the ultrasound element is configured to receive emitted energy that is reflected back from the body lumen.

10. The catheter set forth in claim 1, further comprising hub coupling the proximal ends of the first and second drive shafts to one another.

* * * * *